(12) United States Patent  
Montain et al.

(10) Patent No.: US 7,837,723 B2  
(45) Date of Patent: Nov. 23, 2010

(54) BODY THERMOREGULATION USING SKIN TEMPERATURE FEEDBACK

(75) Inventors: Scott J. Montain, Holliston, MA (US); Tammy J. Doherty, Berghein, TX (US); Samuel N. Cheuvront, Natick, MA (US); Margaret A. Kolka, Uxbridge, MA (US); Lou Ann Stephenson, Uxbridge, MA (US); Bruce S. Cadarette, Burlington, MA (US); Robert Carter, Framingham, MA (US); Michael N. Sawka, Franklin, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 980 days.

(21) Appl. No.: 11/047,339

(22) Filed: Jan. 19, 2005

(65) Prior Publication Data

US 2007/0198072 A1   Aug. 23, 2007

Related U.S. Application Data

(60) Provisional application No. 60/538,140, filed on Jan. 22, 2004.

(51) Int. Cl.
*A61F 7/00* (2006.01)
(52) U.S. Cl. .................................. 607/104; 607/108
(58) Field of Classification Search .................. 607/96, 607/104, 108–112; 165/40, 45
See application file for complete search history.

(56) References Cited

U.S. PATENT DOCUMENTS

| | | | |
|---|---|---|---|
| 3,736,764 A * | 6/1973 | Chambers et al. ............... | 62/89 |
| 3,744,555 A * | 7/1973 | Fletcher et al. ................ | 165/46 |
| 4,034,740 A | 7/1977 | Atherton et al. | |
| 4,718,429 A * | 1/1988 | Smidt ........................... | 607/104 |
| 4,738,119 A | 4/1988 | Zafred | |
| 5,092,129 A | 3/1992 | Bayes et al. | |
| 5,263,336 A * | 11/1993 | Kuramarohit ............... | 62/259.3 |
| 5,269,369 A | 12/1993 | Faghri | |
| 5,871,526 A * | 2/1999 | Gibbs et al. .................. | 607/104 |
| 6,508,831 B1 * | 1/2003 | Kushnir ....................... | 607/104 |

(Continued)

OTHER PUBLICATIONS

Charlie Huzienga et al.; Skin and core temperature response to partial and whole body heating and cooling; Journal of Thermal Biology; 2004; 549-558; vol. 29; Elsevier.

(Continued)

*Primary Examiner*—Roy D Gibson
(74) *Attorney, Agent, or Firm*—Elizabeth Arwine; Marcus A. Streips (57) ABSTRACT

A method and apparatus for cooling a human being utilizes skin temperature feedback to control the amount of cooling. When the measured skin temperature reaches a preset high temperature, the human being is cooled until the measured skin temperature reaches a preset low temperature, and then cooling of the human being stops. In one embodiment, the preset high temperature is about 35 degrees Centigrade and the preset low temperature is about 33 degrees Centigrade. Cooling of the human being resumes whenever the preset high temperature is reached and pauses whenever the preset low temperature is reached to thereby provide intermittent cooling to the human being. The invention is also applicable to heating a human being.

11 Claims, 7 Drawing Sheets

U.S. PATENT DOCUMENTS

| | | | |
|---|---|---|---|
| 6,551,348 B1 * | 4/2003 | Blalock et al. | 607/104 |
| 6,681,589 B2 | 1/2004 | Brudnicki | |
| 6,685,731 B2 * | 2/2004 | Kushnir et al. | 607/104 |
| 7,087,075 B2 * | 8/2006 | Briscoe et al. | 607/104 |
| 7,089,995 B2 * | 8/2006 | Koscheyev et al. | 165/46 |
| 7,179,279 B2 * | 2/2007 | Radons et al. | 607/108 |
| 2003/0013998 A1 | 1/2003 | Augustine | |

OTHER PUBLICATIONS

Andrew J. Young et al; Cooling different body surfaces during upper and lower body exercise; J. Appl. Physiol.; 1987; 1218-1223; vol. 63 No. 3.

Xiaojiang Xu et al; Model of human thermoregulation for intermittent regional cooling; Aviat Space Environ Med; 2004; 1065-1069; vol. 75.

Samuel N. Cheuvront; Efficacy of intermittent, regional microclimate cooling; J Appl Physiol; 2003; 1841-48; vol. 94.

Michael N. Sawka et al; Heat exchange during upper and lower body exercise; J Appl Physiol: Respirat. Environ. Exercise Physiol. 1984; 1050-54; vol. 57 No. 4.

Arsenio Veicsteinas et al; Superficial shell insulation in resting and exercising men in cold water; J Appl Physiol: Respirat Environ Exercise Physiol 1982; 1557-64; vol. 52.

Karen L. Speckman et al; Perspectives in microclimate cooling involving protective clothing in hot enviroments; Int'l J of Industrial Ergonomics 1988; 121-147; vol. 3.

John M. Johnson et al; Regulation of the cutaneous circulation; Fed of Am Societies for Exp Biol Proc 1986; 2841-50; vol. 45 No. 13.

Pablo E. Pergola et al; Control of skin blood flow by whole body and local skin cooling in exercising humans; Am J Physiol 1996; H208-H215; vol. 270.

Pablo E.Pergola et al; Reflex control of active cutaneous vasodilation by skin temperature in humans; Am J Physiol 1994; H1979-H1984; vol. 266.

Xiaojiang Xu et al; Multi-loop control of liquid cooling garment systems; Ergonomics 1999; 282-98; vol. 42 No. 2.

Avraham Shitzer et al; Thermal protective garment using independent regional control of coolant temperature; Aerospace Med 1973; 49-59; vol. 1.

Leo J. Thornley et al; Responsiveness of thermal sensors to nonuniform thermal environments and exercise; Aviat Space Environ Med 2003; 1135-41; vol. 74.

Karen L. Nyberg et al; Model of human/liquid cooling garment interaction for space suit automatic thermal control; Transactions of the ASME 2001; 114-120; vol. 123.

S. H. Constable et al; Intermittent microclimate cooling during rest increases work capacity and reduces heat stress; Ergonomics 1994; 277-285; vol. 37 No. 2.

S. H. Bomalaski et al; Continuous and intermittent personal microclimate cooling strategies; Aviat Space Environ Med 1995; 745-50; vol. 66 No. 8.

Andrea Kurz et al; Thermoregulatory Vasoconstriction Impairs Active Cooling; Anesthesiology; 1995; 870-876; vol. 82 No. 4; United States; Abstract.

R. Stoen et al; The Thermoregulatory Threshold is Inversely Proportional to Isoflurane Concentration; Anesthesiology; 1990; 822-827; vol. 72 No. 5; United States; Abstract.

* cited by examiner

| SUBJECT | ΔHR (0–75 min) (Beats·min⁻¹) | ΔTc (6–75 min) (°C) | Tc–Tsk Gradient (at 75 min) (°C) | Electrical Power (W) |
|---|---|---|---|---|
| CC | | | | |
| MEAN | 26 | 0.49 | 5.7 | 224 |
| SD | 10 | 0.39 | 0.5 | 15 |
| IC | | | | |
| MEAN | 30 | 0.66 | 4.6 | 169 |
| SD | 9 | 0.23 | 0.6 | 16 |
| SKIN TEMPERATURE FEEDBACK | | | | |
| MEAN | 31 | 0.45 | 3.8 | 122 |
| SD | 10 | 0.27 | 0.4 | 18 |

BODY THERMOREGULATION USING SKIN TEMPERATURE FEEDBACK

CROSS-REFERENCE TO RELATED APPLICATIONS

This application claims the benefit of priority of U.S. provisional patent application Ser. No. 60/538,140 filed Jan. 22, 2004, which is hereby incorporated by reference.

STATEMENT OF GOVERNMENT INTEREST

The invention described herein may be manufactured and used by or for the Government of the United States of America for government purposes without the payment of any royalties therefor.

BACKGROUND OF THE INVENTION

The present invention relates in general to methods and devices for regulating body temperature in humans and in particular to methods and devices for regulating body temperature in humans using skin temperature feedback.

Some closely related literature includes, in ascending chronological order: (1) Shitzer, A., Chato, J. C., and Hertig, B. A. Thermal protective garment using independent regional control of coolant temperature. Aerospace Med. 1: 49-59, 1973. (2) Veicsteinas, A, Ferretti, G, and Rennie, D W. Superficial shell insulation in resting and exercising men in cold water. J. Appl. Physiol. 52: 1557-1564, 1982. (3) Sawka, M N, Gonzalez, R R, Drolet, L L, and Pandolf, K B. Heat exchange during upper and lower body exercise. *J. Appl. Physiol.* 57: 1050-1054, 1984. (4) Johnson, J M, Brenglemann, G L, Hales, J R S, Vanhoutte, P M, and Wenger, C B. Regulation of the cutaneous circulation. Federation Proc. 45: 2841-2850, 1986. (5) Speckman, K L, Allan, A E, Sawka, M N, Young, A J, Muza, S R, and Pandolf, K B. Perspectives in microclimate cooling involving protective clothing in hot environments. International Journal of Industrial Ergonomics. 3: 121-147, 1988. (6) Pergola, P E, Kellogg, D L, Johnson, J M, and Kosiba, W. Reflex control of active cutaneous vasodilation by skin temperature in humans. Am. J. Physiol. 266 (Heart Circ. Physiol. 35): H1979-H1984, 1994. (7) Constable, S. H., Bishop, P. A., Nunneley, S. A., and Chen, T. Intermittent microclimate cooling during rest increases work capacity and reduces heat stress. Ergonomics. 37(2): 277-285, 1994. (8) Bomalaski, S. H., Chen, Y. T., and Constable, S. H. Continuous and intermittent personal microclimate cooling strategies. Aviat. Space Environ. Med. 66(8): 745-750, 1995. (9) Pergola, P E, Johnson, J M, Kellogg, D L, and Kosiba, W. Control of skin blood flow by whole body and local skin cooling in exercising humans. Am. J. Physiol. 270 (Heart Circ. Physiol. 35): H208-H215, 1996. (10) Xu, X., Hexamer, M., and Werner, J. Multiloop control of liquid cooling garment systems. Ergonomics. 42(2): 282-298, 1999. (11) Nyberg, K. L., Diller, K. R., and Wissler, E. H. Model of human/liquid cooling garment interaction for space suit automatic thermal control. J. Biomechanical Engineering. 123: 114-120, 2001. (12) Cheuvront, S. N., Kolka, M. A., Cadarette, B. S., Montain, S. J., and Sawka, M. N. Efficacy of intermittent, regional microclimate cooling. J. Appl. Physiol. 94: 1841-1848, 2003. (13) Thomley, L. J., Cheung, S. S., and Sleivert, G. G. Responsiveness of thermal sensors to nonuniform thermal environments and exercise. Aviat. Space Environ. Med. 74: 1135-1141, 2003. (14) Xu, X., Berglund, L. G., Cheuvront, S. N., Endrusick, T. L., and Kolka, M. A. Model of human thermoregulation for intermittent regional cooling. Aviat. Space Environ. Med. 75: 1065-1069, 2004.

Many occupations (e.g., firefighters, soldiers, astronauts, explosive ordnance, toxic waste clean-up) require workers to wear personal protective equipment (PPE) with characteristic high insulation (clo) and low moisture permeability ($i_m$) properties. These conditions impose uncompensable heat stress (required evaporative cooling exceeds evaporative cooling capacity of environment) that results in rapid heat storage and a reduction in work capabilities. Specifically, physical and cognitive performance is severely compromised and heat strain becomes overwhelming in a relatively short period.

Present-day microclimate cooling (MCC) systems are designed to remove heat from the skin using ice-packet vests, cooled air, or by circulating cooled liquid in tubes. Each of these methods is effective in reducing heat strain and extending work performance. For most military, space, and firefighting applications, liquid-cooled systems have several advantages over other MCC approaches, including reduced logistical requirements and sustainable high cooling capacities.

Engineering approaches for developing liquid MCC systems have focused on enhancing MCC efficacy by reducing coolant temperatures or increasing coolant flow. However, these engineering approaches increase MCC power (battery) requirements. Ironically they may also reduce heat transfer potential in certain situations. Skin cooling produces cutaneous vascular constriction that decreases convective heat transfer from the body core to the periphery. Superficial shell insulation (skin and subcutaneous fat) approaches near maximal values at skin temperatures of 30° C., with the onset of vasoconstriction occurring at skin temperatures of 32-33° C. Thus, the heat loss advantage obtained by widening the core-to-skin temperature gradient with constant cooling is progressively reduced by increased superficial shell insulation as skin temperature drops below 32° C.

A primary object of the present invention is to reduce the amount of power required for body cooling and/or heating. This and other objects of the invention are achieved by using skin temperature feedback to control the cooling or heating of the body. In one embodiment, the skin temperature is maintained between a high temperature of about 35 degrees Centigrade and a low temperature of about 33 degrees Centigrade.

Further objects, features and advantages of the invention will become apparent from the following detailed description taken in conjunction with the accompanying drawings.

DETAILED DESCRIPTION OF THE PREFERRED EMBODIMENTS

The inventors were the first to compare the effects of systematic intermittent cooling (IC) to constant cooling (CC) of the skin for improving MCC effectiveness during work in protective clothing. They discovered that the heat flux benefits from periodically (intermittently) applying cooling to warm-vasodilated skin offset the potential for vasoconstriction that occurs with continuous skin cooling. The inventors observed that when skin temperature was maintained between about 33 and 35 degrees Centigrade in IC, thermoregulatory and cardiovascular strain was similar to CC despite less total cooling time with IC. That is to say, this is the temperature range that optimized heat flux by minimizing vasoconstriction, without undue cardiovascular strain, and with an added potential of reducing MCC power (battery) requirements as a consequence of reducing the total required cooling time. The inventors hypothesized that the most efficient MCC system would provide automated cooling on demand using an approximate skin temperature range (33 to 35 degrees Centigrade) as feedback control for perfusion (begin cooling when skin temperature reaches 35 degrees Centigrade) and withdrawal (stop cooling when skin temperature reaches 33 degrees Centigrade).

Figure 1:
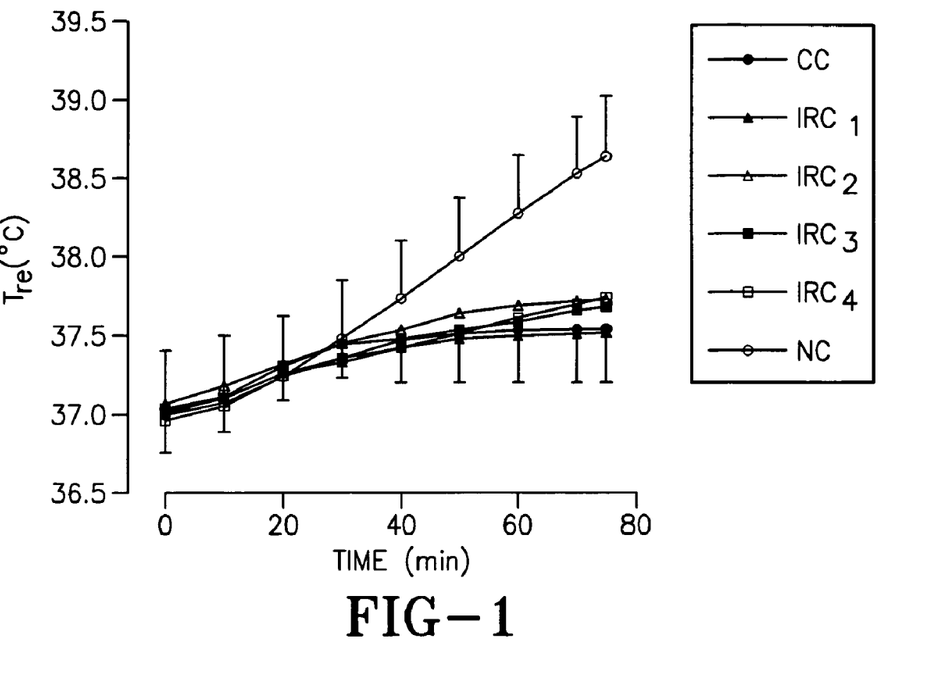
FIG. 1 is a graph of body core temperature (rectal temperature, $T_{re}$) versus time for six cooling paradigms.

FIG. 1 illustrates that IC reduces thermoregulatory strain (rectal temperature) similarly to CC regardless of the systematic IC paradigm used (IRC1-4). When no cooling is provided (NC) rectal temperature rises significantly above all cooling paradigms after 50 minutes of work. From: Cheuvront, S. N., Kolka, M. A., Cadarette, B. S., Montain, S. J., and Sawka, M. N. Efficacy of intermittent, regional microclimate cooling. J. Appl. Physiol. 94: 1841-1848, 2003.

Figure 2:
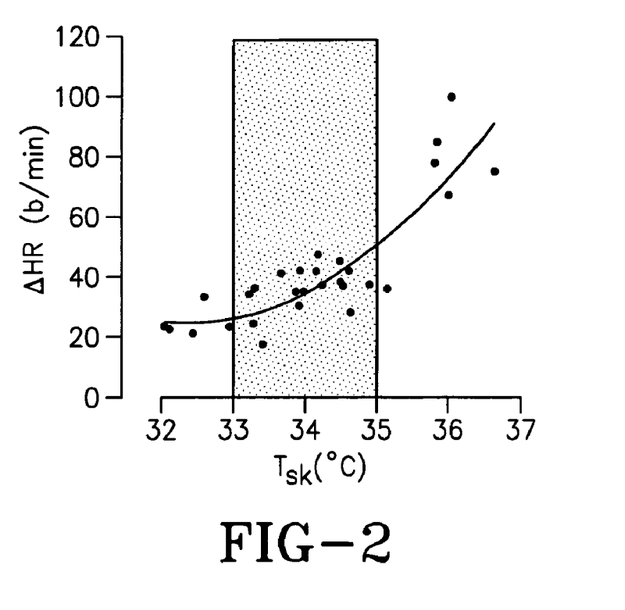
FIG. 2 is a graph of the change in heart rate versus skin temperature.

FIG. 2 illustrates that cardiovascular strain is similar when MCC maintains skin temperature between 32 and 35 degrees Centigrade. When skin temperature exceeds 35 degrees Centigrade, a severe penalty results. The relationship between heart rate change and mean skin temperature is curvilinear [$y=3668+-225.8\,(T_{sk})+3.499\,(T_{sk})^2$]. Shaded area represents temperature band for optimal heat transfer. From: Cheuvront, S. N., Kolka, M. A., Cadarette, B. S., Montain, S. J., and Sawka, M. N. Efficacy of intermittent, regional microclimate cooling. J. Appl. Physiol. 94: 1841-1848, 2003.

An embodiment of a skin temperature feedback MCC system was built and the energy savings hypothesis was tested. CC, IC and skin temperature feedback were compared. All three paradigms resulted in similar thermoregulatory and cardiovascular strain, as well as perceived thermal comfort. Compared with CC, IC and skin temperature feedback reduced power requirements by 25% and 46%, respectively. This reduction in power requirement is a very significant advance in the art of human body thermoregulation.

Figure 3A:
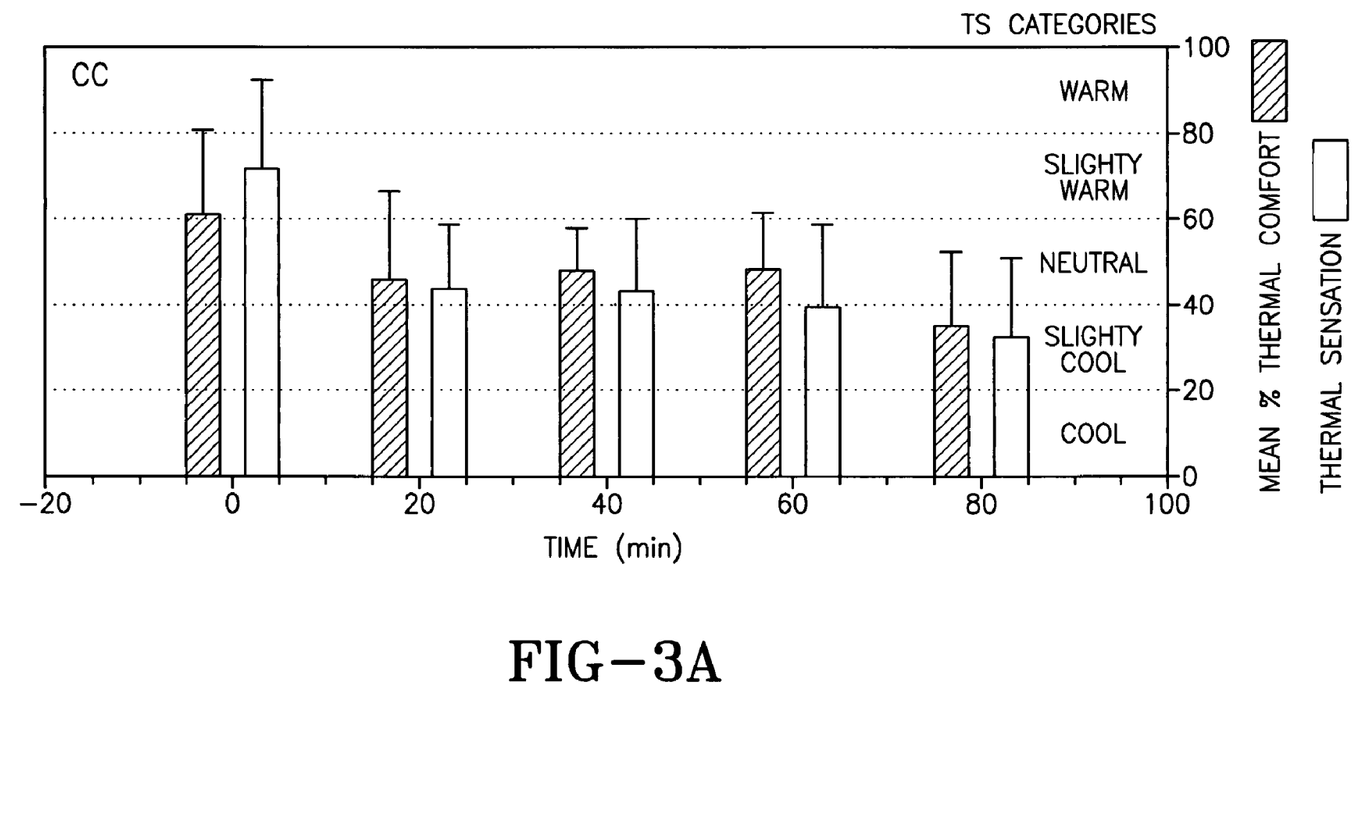
FIGS. 3A-3C are bar graphs of thermal comfort and thermal sensation for three cooling paradigms.
Figure 3B:
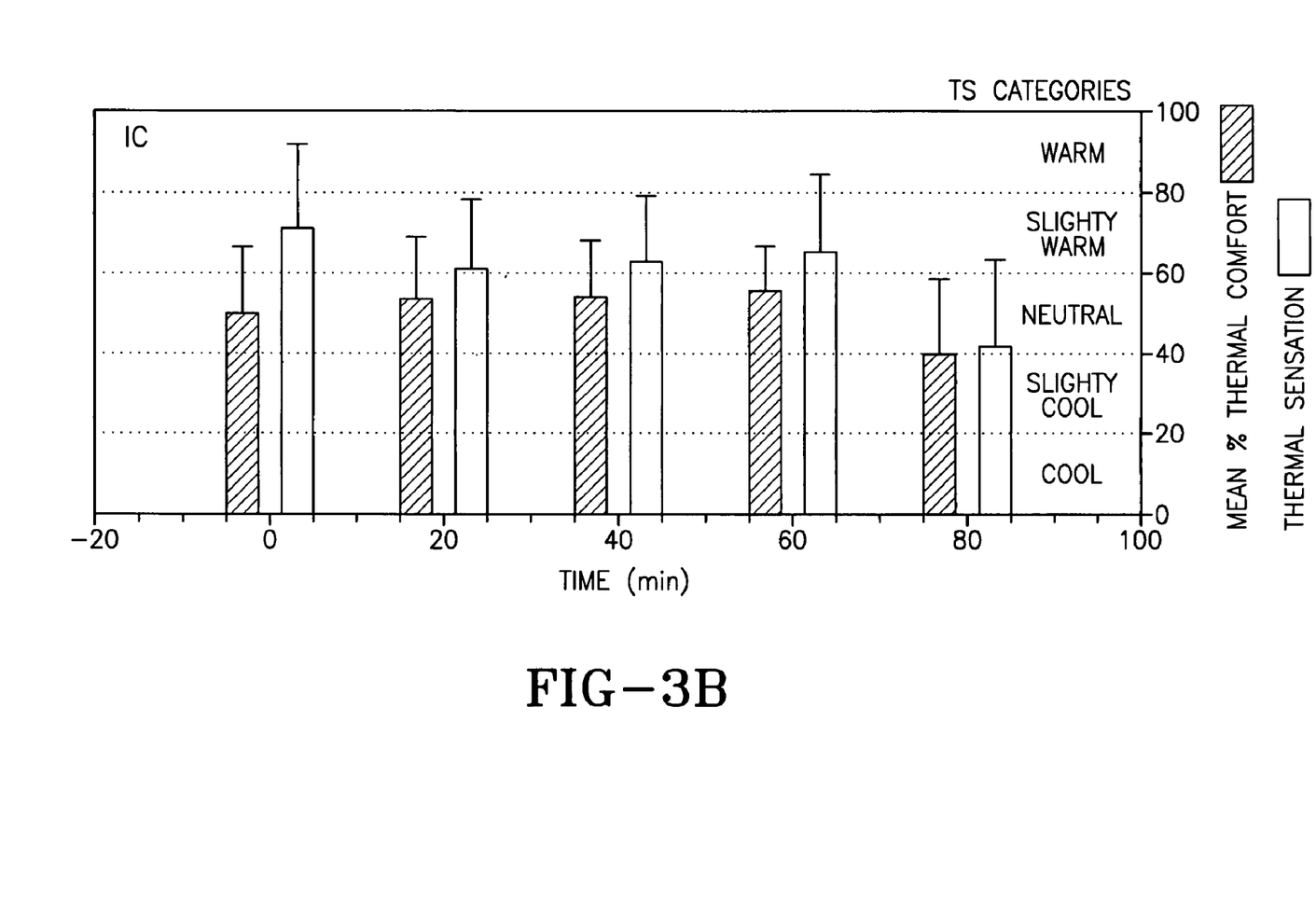
Figure 3C:
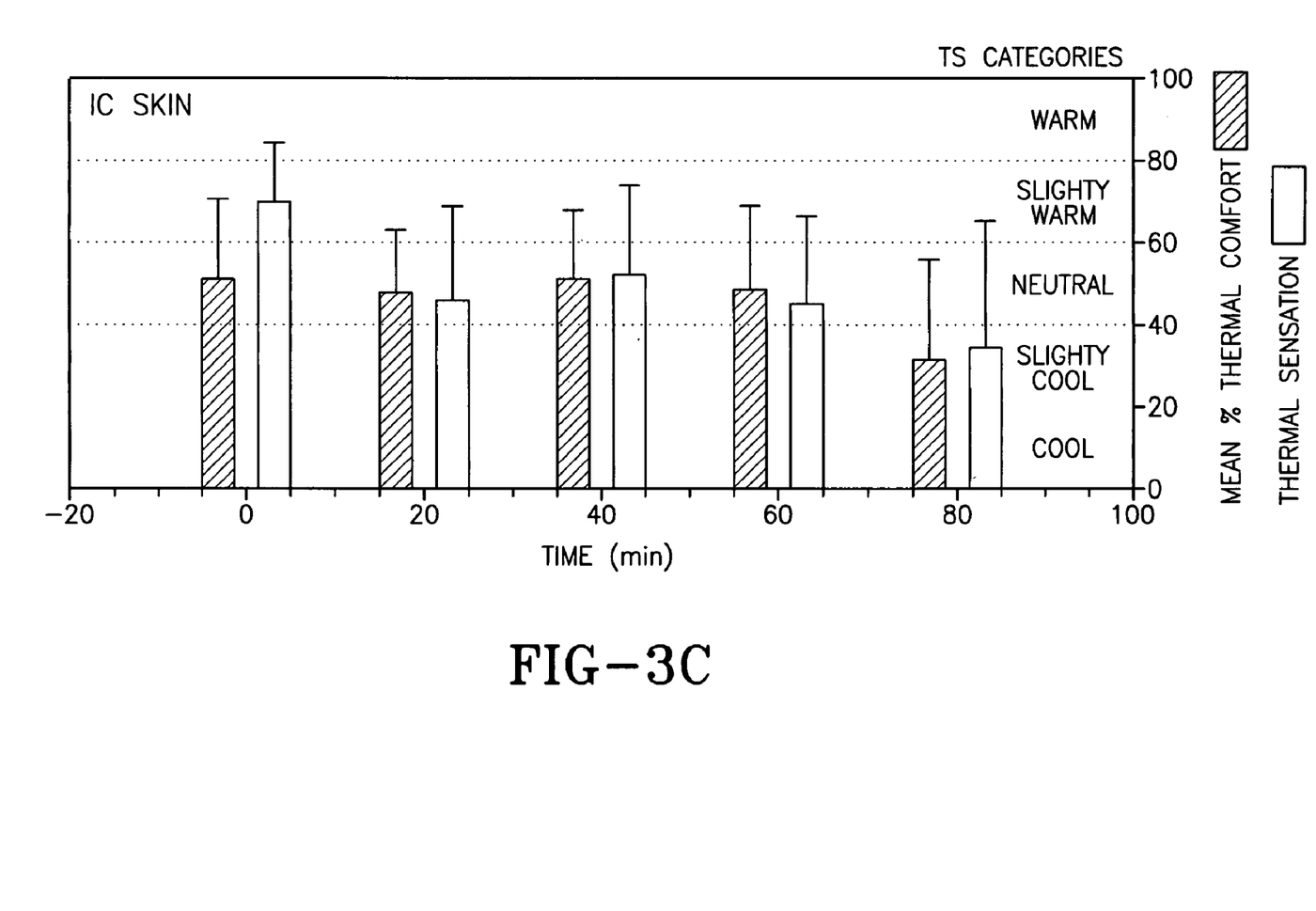

FIGS. 3A-3C illustrate thermal comfort and thermal sensation for three cooling paradigms. FIG. 3A shows constant cooling (CC), FIG. 3B shows intermittent cooling (IC) and FIG. 3C shows intermittent cooling using skin temperature feedback (Icskin). Thermal comfort and sensation are similar among trials. From: Vernieuw, C. R., Stephenson, L. A., and Kolka, M. A., Thermal comfort and sensation in exercising soldiers wearing a microclimate cooling system individually controlled by skin temperature. In preparation for publication.

Figure 4:
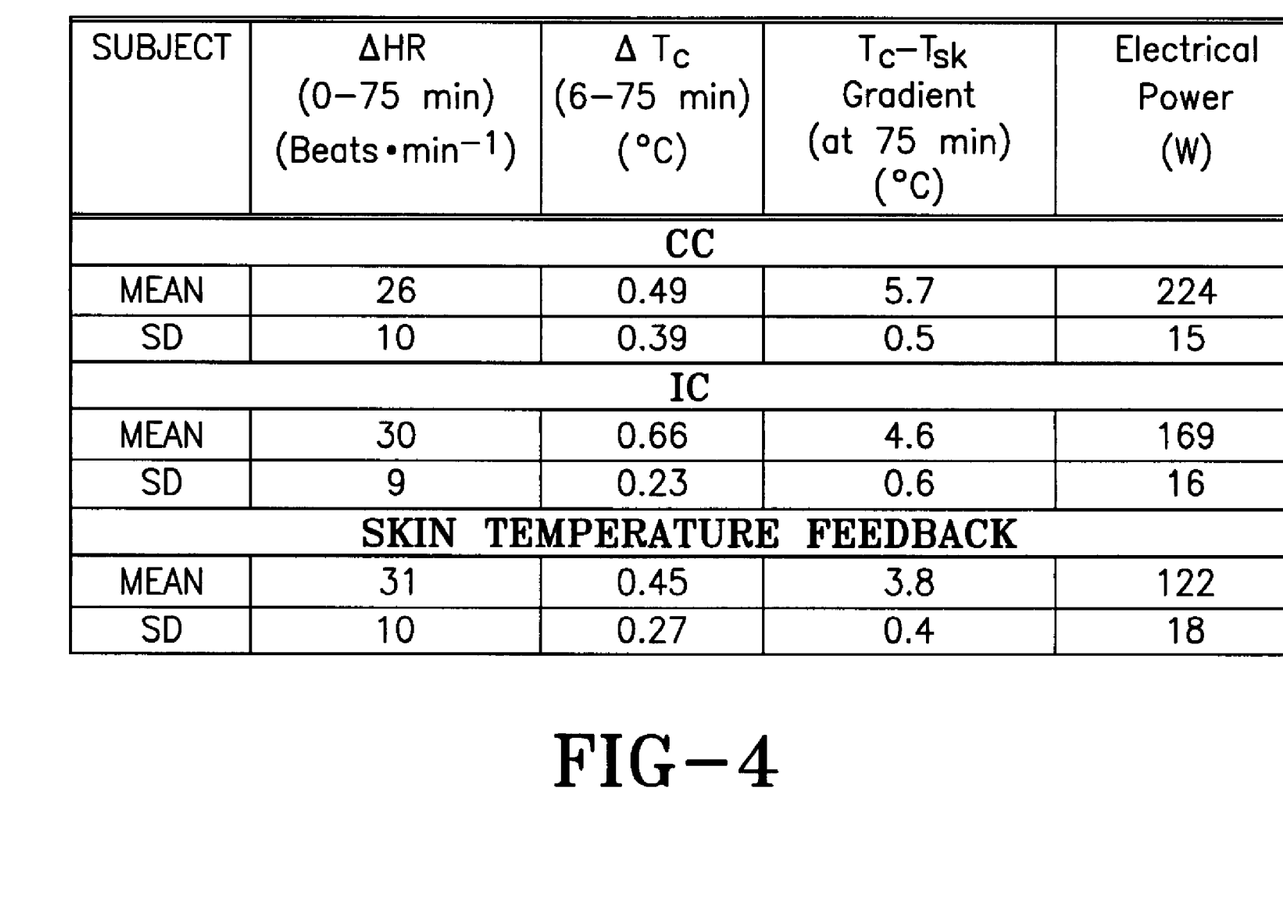
FIG. 4 is a comparison of three cooling paradigms showing mean and standard deviation values for four parameters.

FIG. 4 is a comparison of three cooling paradigms (CC, IC and skin temperature feedback) showing mean and standard deviation values for change in heart rate (delta HR), change in core temperature (delta Tc), difference between core temperature and skin temperature (Tc-Tskin) and electrical power requirements. Thermoregulatory and cardiovascular strain was similar among the three paradigms. Cooling power requirements were reduced by 25% and 46% in IC and skin temperature feedback, respectively, compared with CC. From: Stephenson, L. A., Vernieuw, C. R., Leammukda, W., Teal, W., Laprise, B., Cadarette, B. S., Kolka, M. A., Microclimate cooling activated by skin temperature feedback saves electrical energy. In preparation for publication.

Figure 5A:
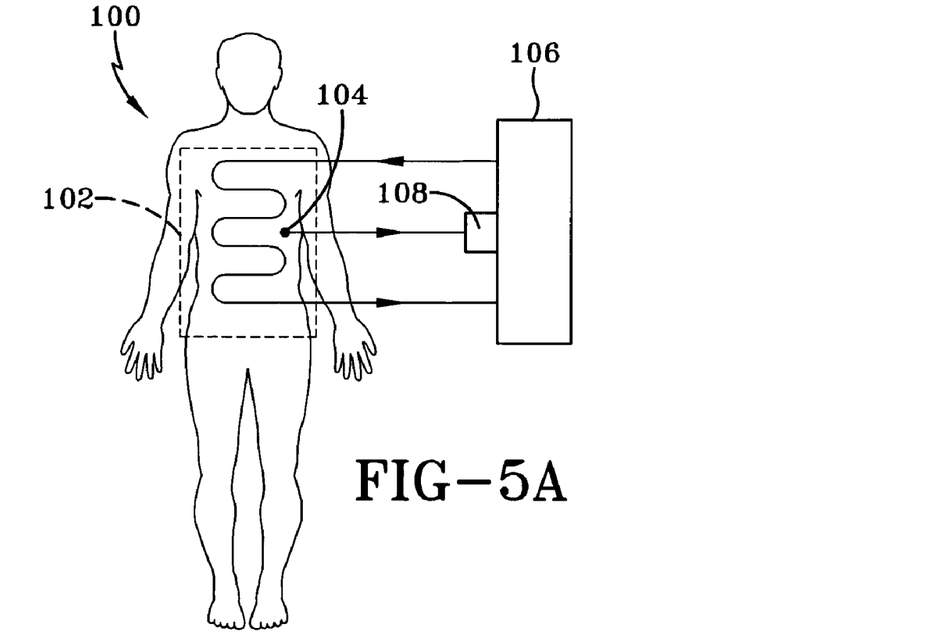
FIG. 5A is a schematic showing cooling of a human being using skin temperature feedback.

FIG. 5A is a schematic showing cooling of a human being 100 using skin temperature feedback. A cooling source 106 is connected to a garment 102 that is worn by the human being 100. The garment 102 extracts heat from the human being 100 by, for example, liquid cooling, air cooling, or phase change. A device 104 for measuring skin temperature, such as a skin thermistor, is connected to a control 108 for the cooling source.

One aspect of the invention is a method of cooling the human being 100 that comprises measuring skin temperature of the human being; and, when the measured skin temperature reaches a preset high temperature, cooling the human being until the measured skin temperature reaches a preset low temperature and then ceasing cooling of the human being, otherwise known as "skin temperature feedback for microclimate cooling."

In one embodiment of the cooling method, the preset high temperature is about 35 degrees Centigrade and the preset low temperature is about 33 degrees Centigrade. Cooling begins when the sensed skin temperature reaches about 35 degrees Centigrade and continues until the sensed skin temperature falls to about 33 degrees Centigrade. The cycle is repeated as necessary.

Figure 5B:
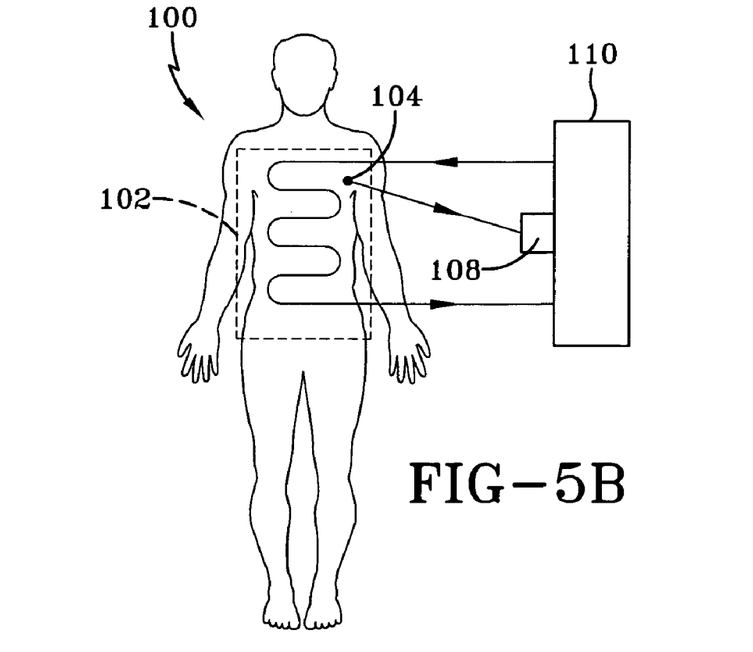
FIG. 5B is a schematic showing heating of a human being using skin temperature feedback.

FIG. 5B is a schematic showing heating of a human being 100 using skin temperature feedback. A heat source 110 is connected to a garment 102 that is worn by the human being 100. The garment 102 adds heat to the human being 100 by, for example, liquid heating, air heating, or phase change. A device 104 for measuring skin temperature, such as a skin thermistor, is connected to a control 108 for the heating source.

Another aspect of the invention is a method of heating a human being 100 that comprises measuring skin temperature of the human being; and, when the measured skin temperature reaches a preset low temperature, heating the human being until the measured skin temperature reaches a preset high temperature and then ceasing heating of the human being, otherwise known as "skin temperature feedback for microclimate heating."

In one embodiment of the heating method, the preset low temperature is about 33 degrees Centigrade and the preset high temperature is about 35 degrees Centigrade. Heating begins when the sensed skin temperature falls to about 33 degrees Centigrade and continues until the sensed skin temperature reaches about 35 degrees Centigrade. The cycle is repeated as necessary.

Figure 6:
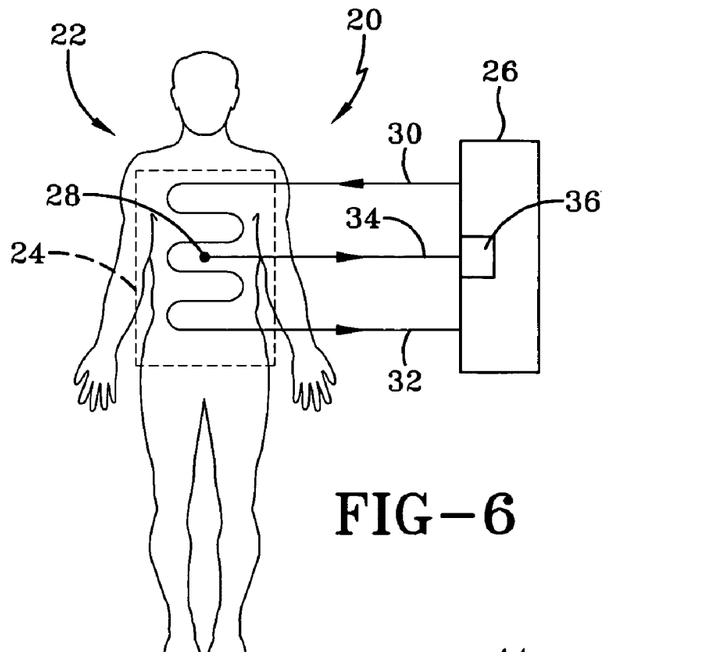
FIG. 6 is a schematic drawing of a body cooling apparatus.

Another aspect of the invention is a body cooling apparatus 20 shown schematically in FIG. 6. Body cooling apparatus 20 includes a cooling garment 24 that is fitted on a human being 22, a cooling source 26, cooling connections 30, 32 between the cooling source 26 and the cooling garment 24, at least one device 28 for measuring skin temperature and an electrical connection 34 between the skin temperature measuring device 28 and a control 36 for the cooling source 26.

Cooling garment 24 may be, for example, a liquid cooling garment, an air cooling garment or a phase change cooling garment. Cooling source 26 may be, for example, a chilled water source, a cold air source, or a source of a phase change refrigerant. In one embodiment, garment 24 is a liquid cooling garment made of, for example, cotton or Nomex® aramid fabric woven or laminated around small diameter Tygon® tubing (2.5 mm, I.D.) divided into multiple parallel circuits. It should be noted that apparatus 20 may be readily adapted for body heating by exchanging a heat source for the cooling source 26.

Figure 7:
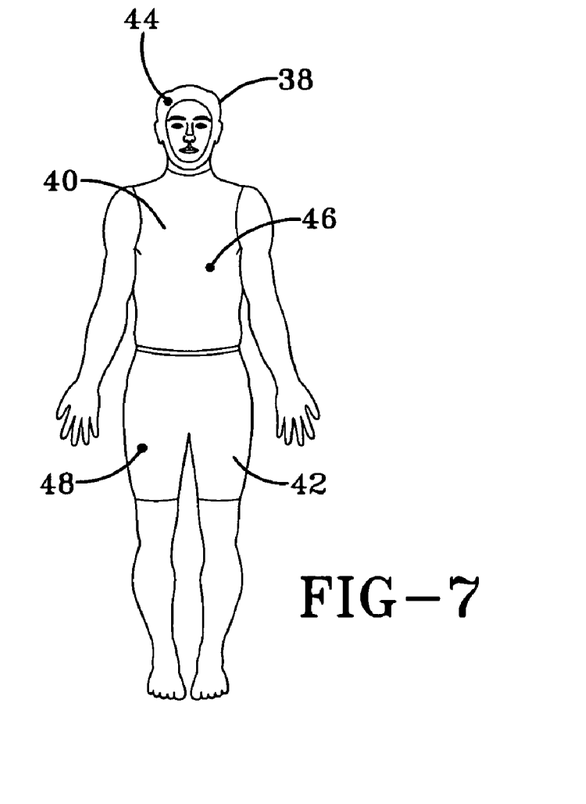
FIG. 7 is a schematic drawing of a portion of a body cooling apparatus.

Garment 24 may be styled to cover any portion of the body. For example, as shown in FIG. 7, there may be a hood section 38 to cover the head, a vest section 40 to cover the torso and a pants section 42 to cover the legs. In an embodiment of the garment 24 that includes a hood section 38, a vest section 40 and a pants section 42, the percentage of body surface area covered is about sixty percent. For improved comfort, heat transfer tubes may be omitted from the crotch and buttocks areas. Preferably, the garment does not cover sensitive wear points such as elbows and the back of the knees.

The device 28 for measuring skin temperature may be, for example, a skin thermistor. A single thermistor or multiple thermistors placed at different locations on the body may be used. In the case of a single thermistor, the skin temperature used to control the cooling source 26 (or heating source) is measured by the single thermistor. If multiple skin thermistors are used, the mean weighted skin temperature may be calculated as 0.30 (upper body skin temperature)+0.20 (lower body skin temperature). See, e.g, Ramanathan, N. L., J. Appl. Physiol., 19: 931-933, 1964. The (upper body skin temperature) is the sum of two measurements on the upper body, for example, the chest and arm or the head and arm (or twice a single measurement). The (lower body skin temperature) is the sum of two measurements on the lower body, for example, the thigh and calf (or twice a single measurement).

By way of example, FIG. 7 shows three thermistors 44, 46 and 48. Assume thermistor 44 on the head reads 33 degrees, thermistor 46 on the chest reads 35 degrees and thermistor 48 on. the thigh reads 36 degrees. Using the above described relation, the mean skin temperature equals 0.30(33+35)+0.20(36+36) which equals 34.8. Other methods for calculating mean skin temperature may, of course, be used.

In one embodiment, cooling source 26 is a chilled water source that includes a heat exchanger and a vapor compression refrigerator. Heat generated by the human 22 is captured by the chilled water circulating through liquid cooling garment 24. The chilled water returns to the chilled water source 26 and rejects the body heat through a heat exchanger to the working fluid of a vapor compression refrigerator. The heat exchanger and vapor compression refrigerator may be carried in a backpack or a belt pack. The refrigerator may be, for example, battery powered or internal combustion engine powered. The control 36 receives the mean skin temperature and controls the flow of chilled water to the liquid cooling garment. When the mean skin temperature reaches about 35 degrees Centigrade, the flow of chilled water is turned on. When the mean skin temperature reaches about 33 degrees Centigrade, the flow of chilled water is turned off. This cycle is repeated as long as cooling is desired. The control 36 may be, for example, a pump in the chilled water lines, a bypass valve that bypasses the heat exchanger, or other devices for controlling cooling systems.

While the invention has been described with reference to certain preferred embodiments, numerous changes, alterations and modifications to the described embodiments are possible without departing from the spirit and scope of the invention, as defined in the appended claims and equivalents thereof.

What is claimed is:

1. A method of cooling a human being, comprising:
   measuring skin temperature of the human being;
   providing a cooling garment and fitting the cooling garment on the human being; and
   when the measured skin temperature reaches a preset high temperature, cooling the human being until the measured skin temperature reaches a preset low temperature and then ceasing cooling of the human being, wherein the preset high temperature is about 35 degrees Centigrade and the preset low temperature is about 33 degrees Centigrade;
   wherein cooling of the human being resumes whenever the preset high temperature is reached and pauses whenever the preset low temperature is reached to thereby provide intermittent cooling to the human being; and
   further wherein the method maximizes an amount of heat transfer per unit of power consumed for cooling the human being compared to continuous cooling methods of cooling human beings.

2. The method of claim 1 wherein the measured skin temperature is determined from a single temperature measuring device.

3. The method of claim 1 wherein the measured skin temperature is determined from a plurality of temperature measuring devices.

4. The method of claim 1 wherein the cooling garment includes a hood section, a vest section and a pants section.

5. The method of claim 1 wherein the cooling garment covers about sixty percent of the body surface area of the human being.

6. A method of heating a human being, comprising:
   measuring skin temperature of the human being;
   providing a heating garment and fitting the heating garment on the human being; and
   when the measured skin temperature reaches a preset low temperature, heating the human being until the measured skin temperature reaches a preset high temperature and then ceasing heating of the human being, wherein the preset high temperature is about 35 degrees Centigrade and the preset low temperature is about 33 degrees Centigrade;
   wherein heating of the human being resumes whenever the preset low temperature is reached and pauses whenever the preset high temperature is reached to thereby provide intermittent heating to the human being; and
   further wherein the method maximizes an amount of heat transfer per unit of power consumed for heating the human being compared to continuous heating methods of heating human beings.

7. A body cooling apparatus for a human being, comprising:
   a cooling garment on the human being;
   a cooling source connected to the cooling garment;
   a skin temperature measuring device located on the human being; and
   a control for controlling the cooling source, the skin temperature measuring device being connected to the control for the cooling source, wherein the cooling source is a chilled liquid source and the cooling garment is a liquid cooling garment and further wherein chilled liquid is supplied to the liquid cooling garment when the skin temperature measuring device senses a preset high temperature of about 35 degrees Centigrade and chilled liquid is not supplied to the liquid cooling garment when the skin temperature measuring device senses a preset low temperature of about 33 degrees Centigrade;
   wherein the body cooling apparatus maximizes an amount of heat transfer per unit of power consumed for cooling the human being compared to continuous cooling apparatus for cooling human beings.

8. The apparatus of claim 7 wherein the skin temperature measuring device comprises a skin thermistor.

9. The apparatus of claim 7 wherein the skin temperature measuring device comprises a plurality of skin thermistors.

10. The apparatus of claim 7 wherein the cooling garment includes a hood section, a vest section and a pants section.

11. A body heating apparatus for a human being, comprising:
- a heating garment on the human being;
- a heat source connected to the heating garment;
- a skin temperature measuring device located on the human being; and
- a control for controlling the heat source, the skin temperature measuring device being connected to the control for the heat source, wherein the heat source supplies heat to the heating garment when the skin temperature measuring device senses a preset low temperature of about 33 degrees Centigrade and the heat source ceases supplying heat to the heating garment when the skin temperature measuring device senses a preset high temperature of about 35 degrees Centigrade;

wherein the body heating apparatus maximizes an amount of heat transfer per unit of power consumed for heating the human being compared to continuous heating apparatus for heating human beings.

* * * * *